USOO5747022A

United States Patent [19]
Slavtcheff

[11] Patent Number: 5,747,022
[45] Date of Patent: May 5, 1998

[54] COSMETIC MASK

[75] Inventor: Craig Steven Slavtcheff, Cheshire, Conn.

[73] Assignee: Chesebrough-Pond's USA Co., Division of Conopco, Inc., Greenwich, Conn.

[21] Appl. No.: 99,880

[22] Filed: Jul. 30, 1993

[51] Int. Cl.$^6$ .................................................... A61K 7/48
[52] U.S. Cl. .................. 424/78.03; 424/401; 514/112.2; 514/113.3; 514/844; 524/379; 524/503; 525/57
[58] Field of Search .................. 424/401, 78.03, 424/772.2; 514/844, 772.3; 524/379, 503; 525/57

[56] References Cited

U.S. PATENT DOCUMENTS

| | | | |
|---|---|---|---|
| 4,640,932 | 2/1987 | Fong et al. | 514/714 |
| 5,026,552 | 6/1991 | Gueret et al. | 424/401 |
| 5,194,253 | 3/1993 | Garrido | 424/78.03 |

FOREIGN PATENT DOCUMENTS

| | | |
|---|---|---|
| 0 309 309 | 3/1989 | European Pat. Off. . |
| 0 514 760 | 11/1992 | European Pat. Off. . |
| 2 659 551 | 9/1991 | France . |
| 2144133 | 2/1985 | United Kingdom . |

OTHER PUBLICATIONS

Abstract of JP 58 004 707 (1983).

*Primary Examiner*—Jyothsan Venkat
*Attorney, Agent, or Firm*—Milton L. Honig

[57] ABSTRACT

A cosmetic composition for forming a peelable skin mask is provided based on a combination of polyvinyl alcohol and a hydrophobically-modified acrylate or methacrylate polymer. Most effective is a combination of two weight grades of polyvinyl alcohol, a low weight grade having a number average molecular weight ranging from about 15,000 to about 27,000 and a high weight grade having a number average molecular weight ranging from about 44,000 to about 65,000. The hydrophobically-modified acrylate or methacrylate polymer preferably is a copolymer formed from a carboxylic monomer and a $C_8$–$C_{30}$ acrylate ester.

5 Claims, No Drawings

5,747,022

COSMETIC MASK

BACKGROUND OF THE INVENTION

1. Field of the Invention

The invention concerns a quick drying composition that when applied to the face will harden into a peelable mask for overnight treatment of skin.

2. The Related Art

Peelable facial masks are well-known in the cosmetic field. Normally such products are applied to the face in the form of a gel or paste. Upon evaporation of volatile solvent; the former gel or paste produces a film over the facial surface. After a certain period of contact, usually 15–30 minutes, the film is removed by washing with warm water or by being peeled off.

A mask is considered to have an absorption effect for removing unwanted oils from the stratum corneum. Removal of the mask is believed to assure deep cleansing of the skin, in particular of the horny layer of the epidermis. It also provides a state of hyper-hydration of the epidermis, resulting in an improvement in skin tone and texture.

Among the commercially available mask forming products is a clear gel from Revlon Corporation known as "Honey Masque". The listed contents include water, ethyl alcohol, polyvinyl alcohol/vinyl acetate copolymer, dimethicone copolyol, propylene glycol, PEG-8, honey, oleth-10 phosphate, fragrance, preservative and colors. The dry-down time (when the film becomes nontacky) of this particular gel ranges from 15 to 30 minutes. A product sold by the Procter & Gamble Company under the trademark of "Noxzema® Deep Cleansing Mask" is based upon a polyvinyl alcohol film-forming material solubilized in ethanol; other ingredients include sorbitol, PEG-4 steareth-20, PEG-32, PEG-6, preservatives, fragrance, essential oils and colors. Dry-down time for this product is at least 15 minutes.

Masks currently marketed are not designed for nighttime use. A product used at night should dry-down quickly so that the product can be applied within five minutes before going to bed. If the product does not dry quickly, a user is required to be vigilant against contact that might disturb the maturating mask. An ideal product should dry quickly forming a protective crust that prevents the product from being rubbed off on the bed linen.

As noted above, polyvinyl alcohol films have been employed in commercial products. Not only is the dry-down time too slow but these films also do not adhere well to the skin. Polyvinyl alcohol films taught by the known art would fall off during the night.

U.S. Pat. No. 4,640,932 (Fong et al) describes a facial mask based on inorganic thickening agents, absorbent powders and/or organic gelling agents. Suitable as gelling agents are gelatin, starch, cellulosic gums, guar gum, alginates and polyvinyl alcohols. Benzoyl peroxide is present as an active to control or at least mitigate acne vulgaris. Moreover, this product form is different, as it is intended to be immediately washed off. Neither does this type of product form a protective crust or rigid film, thereby rendering it impractical for use during the sleeping hours.

U.S. Pat. No. 5,026,552 (Gueret et al) discloses a mask formed from a mesh of woven fabric and a hydratable gel confined within holes of the mesh. Since the gel is confined, the mask can be pulled off all in one piece thereby performing a skin sloughing treatment.

U.S. Pat. No. 5,194,253 (Garrido et al) describes a method of forming a cosmetic treatment mask based on at least one hydrophilic film-forming polymer, ammonium hyaluronic acid, mineral or organic salt of deoxyribonucleic acid and water. Drying times with this technology are also relatively slow.

Accordingly, it is an object of the present invention to provide a cosmetic mask that is faster drying than similar products heretofore known to the art.

It is another object of the present invention to provide a cosmetic mask that has improved adhesion to the skin.

It is a further object of the present invention to provide a cosmetic mask that in the gel or paste form has improved stability, especially under freeze/thaw cycle storage conditions.

It is still a further object of the present invention to provide a cosmetic mask that can deliver active ingredients to counteract the effects of acne, pimples, redness and blemishes.

These and other objects of the present invention will become more readily apparent from consideration of the following summary, detailed description and examples which follow.

SUMMARY OF THE INVENTION

A composition for forming a cosmetic mask is provided that includes:

(i) at least one polyvinyl alcohol polymer having a number average molecular weight ranging from about 5,000 to about 200,000; and (ii) a hydrophobically-modified acrylate or methacrylate polymer, the polyvinyl alcohol and hydrophobic acrylate or methacrylate polymer being present in a relative weight ratio from about 50:1 to about 1:100.

Advantageously, the polyvinyl alcohol is present as a combination of low and high molecular weight materials of less than 30,000 and more than 40,000, respectively. Preferably, the number average molecular weights for the low and high materials may range from about 15,000 to 27,000 and from about 44,000 to 65,000, respectively.

The hydrophobically-modified polymer is preferably a copolymer having a major portion formed from a monoolefinically unsaturated carboxylic acid or anhydride monomer of 3 to 6 carbon atoms and a minor portion formed from a long chain acrylate or methacrylate ester monomer.

DETAILED DESCRIPTION

Now it has been found that exceptionally short dry-down times of less than 15 minutes can be achieved with a selected combination of a film-forming and an adhesion promoting polymer. Indeed, with the special combination of polymers, the dry-down times are often less than five minutes.

The first necessary polymer is at least one polyvinyl alcohol (PVA). This category of material may be selected from a polymer having a number average molecular weight ranging from about 5,000 to about 200,000. Advantageously, there will be present both a low and high molecular weight polyvinyl alcohol. The former can have a number average molecular weight of less than 30,000, but preferably ranging from about 15,000 to 27,000. The later can have a number average molecular weight of more than 40,000, but preferably ranging from about 44,000 to 65,000. Representative of the low molecular weight range is a material known as Airvol 205S having a viscosity of 5.2–6.2 cps in 4% aqueous solution at 20° C. The high molecular weight material is commercially available as Airvol 523 having a viscosity of 23–27 cps in 4% aqueous solution at 20° C. Airvol products are available from the Air Products Company, Allentown, Pa. Total amount of polyvinyl alcohol may range from about 2 to about 40%, preferably from about 10 to about 20%, optimally between about 12 and 15% by weight. In the embodiment where low and high molecular weight polyvinyl alcohol Is employed, the ratio of the two may range from about 1:20 to 20:1, preferably from about 1:10 to 1:1, optimally from about 1:5 to 1:3, respectively.

Dry PVA films tend not to adhere very well to skin. For an overnight product, the film should stay on the skin throughout the night. It has now been found that excellent adhesion can be achieved with a hydrophobically-modified acrylate or methacrylate polymer. This second critical component of the mask-forming composition is preferably a copolymer formed from a carboxylic monomer in an amount from about 50 to 99% by weight and a long chain acrylate ester monomer in an amount from about 1 to 50% by weight. Amounts of the carboxylic monomer and the acrylate ester monomer are based on the combined weight of both components. It should be understood that more than one carboxylic monomer and more than one acrylate ester can be used in the monomer charge.

The above-mentioned copolymers can be prepared from a monomeric mixture containing two essential monomeric ingredients, each in certain proportions, one being a monomeric olefinically-unsaturated carboxylic monomer of 3 to 6 carbon atoms and the other being an acrylic ester having a long chain $C_8-C_{30}$ aliphatic group. Optionally, there is included in the monomeric mixture a crosslinking monomer. Amount of the carboxylic monomer is generally in a major proportion whereas the acrylic ester is used in a minor proportion. In a preferred embodiment, amount of the carboxylic monomer is 80 to 99%, but especially 90 to 98% by weight, whereas amount of the acrylate monomer is from 20 down to 1%, especially 10 down to 2% by weight, based on the weight of the two monomers.

The copolymers of a carboxylic monomer and an acrylic ester having a long chain aliphatic group can have polymerized therein a minor proportion of a lower alkyl ester of acrylic acid, such as ethyl acrylate, in an amount of 0–40% by weight, preferably 5–30%, based on the total monomer charge.

The preferred carboxylic monomers for use in the copolymer are the monoolefinic acrylic acids having the general structure:

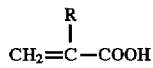

wherein R is a substituent selected form the group consisting of hydrogen, halogen, hydroxyl, lactone, lactam, and the cyanogen (—C—N) groups, monovalent alkyl radicals, monovalent alkaryl radicals and monovalent cycloaliphatic radicals. Of this class, acrylic acid itself is most preferred because of its generally lower cost, ready availability, and ability to form superior polymers. Another particularly preferred carboxylic monomer is maleic anhydride.

The preferred acrylic ester monomers having long chain aliphatic groups are derivatives of acrylic acid represented by the formula:

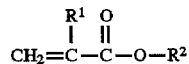

wherein $R^1$ is selected from hydrogen, methyl and ethyl groups and $R^2$ is selected from alkyl groups having from 8 to 30 carbon atoms and oxyalkylene and carbonyloxyalkylene groups, preferably alkyl groups of 10 to 22 carbon atoms. The oxyalkylene and carbonyloxyalkylene groups are particularly oxyethylene and carbonyloxyethylene groups. Representative higher alkyl acrylic esters are decyl acrylate, lauryl acrylate, stearyl acrylate, behenyl acrylate and myristyl acrylate, and the corresponding methacrylates.

The copolymers described herein, when tested in the form of 0.2% aqueous mucilages, have viscosity of 100 to 50,000 cps, preferably 250 to 40,000 cps and especially 500 to 35,000 cps. In the form of 1.0% aqueous mucilages, they have viscosity of 1,000 to 100,000 cps, preferably 2,000 to 90,000 cps, and especially 2,500 to 85,000 cps. These viscosities are measured using a Brookfield RVT Model Viscometer at spindle speed of 20 rpm in the pH range of 7.2 to 7.6.

Commercially the copolymers as described above are available from the B.F. Goodrich Company under the trademark Pemulen TR-2®. The CTFA name is acrylates/ $C_{10}-C_{30}$ alkyl acrylate cross-polymer.

Amounts of the hydrophobically-modified acrylate or methacrylate polymer will range from about 0.1 to about 20%, preferably from about 0.5 to about 5%, more preferably from about 1 to about 2%, optimally between about 1.35 and 1.5% by weight.

The total amount of polyvinyl alcohol to hydrophobically-modified acrylate or methacrylate polymer will range from about 50:1 to 1:100, preferably from about 20:1 to 1:1, optimally between about 12:1 to 8:1, respectively.

Water will also be present in the compositions of the present invention. The amount of water will range from about 10 to about 70%, preferably from about 30 to about 55%, optimally between about 35 and 45% by weight.

Since water is the primary vehicle for delivery of the film-forming polymer, the relative weight ratio can be of significance. Water to total polyvinyl alcohol should range from about 100:1 to about 1:1, preferably from about 10:1 to 2:1, optimally between about 4:1 and 3:1 by weight.

Evaporative solvents to achieve the dry-down of the film-forming polymer onto the skin are also important. Monohydric $C_1-C_3$ alkanols are most suitable with preference being for ethyl alcohol. The amount of monohydric alcohol may range from about 5 to about 50%, preferably from about 15 to about 40%, optimally between about 25 and 35% by weight.

Compositions of the present invention can include a variety of anti-irritancy agents. These may either be water-soluble or water-insoluble (i.e. oil-soluble). Among suitable water-soluble anti-irritancy agents are the salts of glycyrrhizinic acid, especially the alkalimetal and ammonium salts. Representative of the water-insoluble anti-irritancy agents are α-bisabolol (derived from chamomile) and azulene (derived from yarrow). These can be present either as natural extracts or synthetically derived materials ranging in amounts from about 0.0001 to about 5%, preferably from about 0.001 to about 1%, optimally between about 0.01 to about 0.5% by weight. Most especially preferred is dipotassium glycyrrhizinate. Amounts of this category of material may range from about 0.001 to about 3%, preferably between about 0.1 to about 0.5%, optimally between about 0.15 and 0.2% by weight.

Two classes of keratolytic agents may also be effectively used in compositions of the present invention, The first category is represented by $C_7-C_{30}$ β-hydroxy carboxylic acids and their salts. Illustrative of this category is salicylic acid as well as the alkalimetal and ammonium salts thereof. Suitable amounts of salicylic acid or salt may range from about 0.1 to about 10%, preferably between about 0.8 and about 2.5%, optimally between about 1 and 1.5% by weight.

The second class of keratolytic agent is the $C_1$–$C_{25}$ α-hydroxy alkanoic 20 acids. Illustrative of this group of materials are glycolic, lactic, 2-hydroxy-octanoic acids and salts thereof. The salts may be selected from alkalimetal, ammonium and $C_1$–$C_{20}$ alkyl or alkanol ammonium counterions. Levels of α-hydroxyalkanoic acids may range from about 0.1 to about 10%, preferably between about 0.2 and 1%, optimally between about 0.4 and 0.5% by weight.

Antimicrobial agents may also be useful in compositions of the present invention. Typically the antimicrobial agent may be material such as triclosan tricarbanilide, tea tree oil, farnesol, farnesol acetate, hexachlorophene, $C_4$–$C_{20}$ quaternary ammonium salts such as benzolconium chloride and a variety of zinc or aluminum salts. Typically the zinc or aluminum salts are compounds such as zinc pyridinethione, zinc sulphate, zinc chloride, zinc phenolsulphonate, aluminum chloride, aluminum sulphate and aluminum chlorhydrate. Amounts of the astringent may range from about 0.1 to about 5%, preferably from about 0.2 to about 1%, optimally about 0.3% by weight.

A still further component of compositions according to the present invention may be $C_1$–$C_{10}$ alkyl lactates. Most preferred is ethyl lactate which may be present in amounts ranging from about 0.01 to about 5%, preferably between about 0.5 and 3%, optimally between about 1.5 and 2.5% by weight.

A variety of herbal extracts may be included as components of the composition. These extracts may include but are not limited to those of thyme, rosemary, myrrh, bitter orange, coltsfoot and sage. Each of these may range in an amount anywhere from about 0.00001 to about 2%, preferably between about 0.01 and about 0.5% by weight.

Compositions of the invention preferably also contain aloe extract to assist with skin adhesion. Aloe extract levels may range from about 0.01 to about 5%, preferably from about 0.05 to 1%, optimally between 0.1 and 0.75% by weight.

Emollient materials in the form of silicone oils and synthetic esters may be incorporated into compositions of the present invention. Amounts of the emollients may range anywhere from about 0.1 to about 30%, preferably between about 1 and 20% by weight.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalklyaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25°°C.

Among the ester emollients are:

(1) Alkenyl esters of fatty acids having 10 to 20 carbon atoms. Examples thereof include oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate.

(5) Sterols esters, of which cholesterol fatty acid esters are examples thereof.

Most preferred from the foregoing list of esters are PEG-40 hydrogenated castor oil (available as Cremophore RH40®) and PPG-10-cetyl ether (available as Procetyl-10®).

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Thickeners/viscosifiers in amounts up to about 5% by weight of the composition may also be included. As known to those skilled in the art, the precise amount of thickeners can vary depending upon the consistency and thickness of the composition which is desired. Exemplary thickeners are xanthan gum, sodium carboxymethyl cellulose, hydroxyalkyl and alkyl celluloses (particularly hydroxypropyl cellulose), and cross-linked acrylic acid polymers such as those sold by B.F. Goodrich under the Carbopol trademark.

The following examples will more fully illustrate the embodiments of this invention. All parts, percentages and proportions referred to herein and in the appended claims are by weight unless otherwise indicated.

EXAMPLE 1

Typical compositions of the Invention prepared from a water (A), alcohol (B) and oil (C) phases are presented In Table I below.

TABLE I

| INGREDIENT | A | B | C | D | E | F |
|---|---|---|---|---|---|---|
| | | Phase A | | | | |
| Zinc sulphate | 0.300 | 0.600 | 0.300 | — | — | 0.300 |
| Polyvinyl alcoholPVA-205 | 5.100 | 2.800 | 2.800 | 6.000 | 6.000 | 10.000 |
| Polyvinyl alcoholPVA-523 | 5.100 | 10.000 | 10.000 | 4.000 | 4.000 | 2.800 |
| PEG-20M | 0.100 | 0.100 | 0.100 | — | 0.100 | 0.100 |
| Aloe 40x | 0.750 | 0.750 | 0.750 | 0.500 | 0.250 | 1.000 |
| Propylene glycol | 4.000 | — | 4.000 | 4.000 | 4.000 | 2.000 |
| Glycerol | — | 4.000 | — | — | 1.000 | — |
| Cellulose gum 7HF | — | 0.100 | — | — | — | — |
| PEG-6 | — | — | — | 1.000 | — | — |
| PEG-4 | — | — | — | 1.000 | — | — |
| Dipotassium glycyrizzinate | 0.200 | 0.500 | 0.150 | 0.250 | 0.4000 | 0.100 |
| Water | Balance | Balance | Balance | Balance | Balance | Balance |
| | | Phase B | | | | |
| Alcohol SD-40 | 30.020 | 27.770 | 29.220 | 10.250 | 5.100 | 38.730 |
| Salicylic acid | 0.750 | 1.500 | 1.000 | 0.250 | 1.000 | 1.000 |
| Glycolic acid | 0.400 | 0.400 | 0.600 | 3.000 | — | 0.300 |
| Lactic Acid | — | — | — | — | 1.000 | 0.300 |
| Ethyl lactate | 1.500 | 3.000 | 1.500 | — | 1.500 | 1.500 |
| Myrth HS | 0.200 | 1.000 | 0.500 | 0.200 | 0.200 | 0.200 |
| Rosemary HS | 0.200 | 1.000 | 0.500 | 0.200 | 0.200 | 0.200 |
| Coltsfoot HS | 0.200 | 0.500 | 0.500 | 0.200 | 0.200 | 0.200 |
| Sage HS | 0.200 | 0.500 | 0.500 | 0.200 | 0.200 | 0.200 |
| Bitter orange HS | 0.200 | 0.500 | 0.500 | 0.200 | 0.200 | 0.200 |
| Thyme HS | — | | | 0.200 | — | — |
| Yarrow HS | 0.200 | 0.500 | 0.500 | — | 0.200 | 0.200 |
| Pemulen TR-2 | 1.300 | 1.300 | 1.300 | 5.000 | 5.000 | 1.300 |
| Cremophore RH40 | 1.600 | 1.600 | 1.800 | 1.800 | 2.000 | 2.000 |
| Procetyl-10 | 0.800 | 0.80 | 0.900 | 0.900 | 1.000 | 1.000 |
| α-bisabolol | 0.500 | 0.500 | 0.500 | 0.500 | 1.000 | 0.100 |
| Vitamin E acetate | 0.400 | 0.400 | 0.400 | 0.400 | 0.400 | 0.400 |
| Vitamin E linoleate | — | — | 0.100 | 0.100 | 0.100 | 0.100 |
| Vitamin A palmitate | 0.50 | 0.50 | — | — | — | — |
| Tea tree oil | 0.80 | 0.80 | 0.80 | 0.40 | 0.40 | 0.40 |
| Eucalyptus oil | — | — | — | 0.80 | — | — |

*HS indicates a 2% by weight dry extract in propylene glycol.

EXAMPLE 2

A series of experiments were conducted to determine the optimum combination of firm-forming and adhesive polymers. These were evaluated for facial adhesion, freeze/thaw stability and dry-down time.

TABLE II

Evaluation of Face Mask Formulations

| TEST NO. | MATERIALS | ADHESION* | FREEZE/THAW* STABILITY | DRY-DOWN TIME (MIN.) |
|---|---|---|---|---|
| 1 | 8% PVA-523, 8% PVP | P | P | 8 |
| 2 | 15% PVA-523 | P | P | 15 |
| 3 | 4.75% PVP/VA, 12% PVA | P | P | 12 |
| 4 | 12% PVA-523, 2% GANEX V220 | P | P | 5 |
| 5 | 8% PVA-523, 8%, GAFFIX VC-713 | P | P | 7 |
| 6 | 3% PVP/VA, 16% HPC-HF | E | P | 20 |
| 7 | 7% PVA-523, 10% PVP/VA, 10% PVP | E | P | 13 |
| 8 | 12% PVA-523, 4% PVP/VA, 3% GANEX V220 | P | P | 3 |
| 9 | 12% PVA-523, 4% PVP/VA, 4% GAFQUAT 755N | P | P | 3 |
| 10 | 9% PVA-523, 2% POLYMER JR400 | P | P | 20 |
| 11 | 12% PVA-523, 6% PVP/VA, 1% GANEX V-220, 2% FLEXAN 130 | G | P | 15 |
| 12 | 11% PVA-523, 1% CARBOPOL-1382 | G | P | 5 |
| 13 | 12% PVA-523, 3% GAFFIX VC-713, .75% PEMULEN TR-2 | P | P | 10 |
| 14 | 12% PVA-523, 3% GAFFIX VC-713, .75% PEMULEN TR-2, 1% DERMACRYL-79 | P | P | 12 |
| 15 | 15% PVP/VA, 1.5% PEMULEN TR-2 | P | P | 20 |
| 16 | 9% PVA-523, 1.4% PEMULEN TR-2 | E | P | 5 |
| 17 | 1.5% HPC-HF, 1.5% PEMULEN TR-2 | E | E | 25 |

TABLE II-continued

Evaluation of Face Mask Formulations

| 18 | 10% PVA-523, 1.2% PEMULEN TR-2 | G | P | 3 |
|---|---|---|---|---|
| 19 | 10% PVA-523, 1.% PEMULEN TR-2 | G | P | 3 |
| 20 | 8% PVA-523, 1.0% PEMULEN TR-2 | G | P | 2.5 |
| 21 | 9% PVA-523, .4% CELLULOSE GUM-7HF, 1.4% PEMULEN TR-2 | E | P | 7 |
| 22 | 9% PVA-523, .75% NATROSOL PLUS, 1.4% PEMULEN TR-2 | E | P | 15 |
| 23 | 9% PVA-523, .75% CMHEC-420H, 1.4% PEMULEN TR-2 | E | P | 15 |
| 24 | 9% PVA-523, .5% VEEGUM ULTRA, 1.4% PEMULEN TR-2 | P | P | 12 |
| 25 | 9% PVA-523, 2% GELATIN (40% AQ), 1.3% PEMULEN TR-2 | E | P | 9 |
| 26 | 9% PVA-523, 1% PECTIN, 1.3% PEMULEN TR-2 | E | P | 15 |
| 27 | 9% PVA-523, .5% ALOE 40X, 1.37% PEMULEN TR-2 | E | P | 3.5 |
| 28 | 9% PVA-523, .75% ALOE 40X, 1.3% PEMULEN TR-2, 2.5% PVA-205 | E | E | 3 |
| 29 | 10% PVA-523, .75% ALOE 40X, 1.3% PEMULEN TR-2, 4.0% PVA-205 | E | E | 3.5 |
| 30 | 9.5% PVA-523, .75% ALOE 40X, 1.35% PEMULEN TR-2, 3.5% PVA-205 | E | E | 3 |

*P = poor; G = good; E = excellent

IDENTIFICATION OF MATERIALS IN TABLE (II):

| PVA-523 | Polyvinyl alcohol, high molecular weight |
|---|---|
| PVA-205 | Polyvinyl alcohol, low molecular weight |
| PVP | Polyvinylpyrrolidone |
| Ganex V220 | Polyvinylpyrrolidone/eicosene copolymer |
| Gaffix VC-713 | Vinyl caprolactam/PVP/dimethylamninoethyl methacrylate copolymer |
| HPC-HF | Hydroxypropylcellulose, high molecular weight |
| PVP/VA | Polyvinylpyrrolidone/vinyl acetate copolymer |
| Gafquat 755N | Polyquaternium-11 |
| Polymer JR-400 | Polyquaternium-10 |
| Flexan 130 | Sodium polystyrene sulfonate |
| Carbopol 1382 | Acrylates/$C_{10}$-$C_{30}$ alkyl acrylate crosspolymer |
| Pemulen TR-2 | Acrylates/$C_{10}$-$C_{30}$ alkyl acrylate crosspolymer, more hydrophobically modified |
| Dermacryl-79 | Acrylates/octylacrylamide copolymer |
| Cellulose Gum 7HF | Cellulose gum, medium molecular weight |
| Natrosol Plus | Cetyl hydroxyethylcellulose |
| CMHEC 420H | Carboxymethyl, carboxyethyl cellulose |

The foregoing description and examples illustrate selected embodiments of the present invention. In light thereof, various modifications will be suggested to one skilled in the art, all of which are within the spirit and purview of this invention.

What is claimed is:

1. A composition for forming a peelable cosmetic mask comprising:

(i) a polyvinyl alcohol polymer having a number average molecular weight ranging from about 5,000 to about 200,000; and (ii) a hydrophobically-modified acrylate or methacrylate polymer, the polyvinyl alcohol and hydrophobically-modified acrylate or methacrylate polymer being present in a relative weight ratio from about 20:1 to about 1:1, and the polymer being a copolymer formed from a monoolefinically unsaturated carboxylic acid or anhydride monomer of 3 to 6 carbon atoms in an amount from about 50 to 99% by weight and a $C_{10}$-$C_{30}$ alkyl acrylate ester in an amount from about 1 to about 50% by weight.

2. A composition according to claim 1, wherein the polyvinyl alcohol includes a lower weight portion having a number average molecular weight ranging from about 15,000 to about 27,000 and a higher weight portion having a number average molecular weight range from about 44,000 to 65,000, the lower and higher weight portions being present in a weight ratio of about 1:20 to about 20:1, respectively.

3. A composition according to claim 2, wherein the ratio of lower and higher weight portions ranges from about 1:10 to about 1:1.

4. A composition according to claim 1, wherein water is present from about 30 to about 55% by weight.

5. A composition according to claim 1, further comprising a volatile solvent which is a $C_1$-$C_3$ monohydric alcohol present in an amount from about 5 to about 50% by weight.

* * * * *